United States Patent [19]

Drake

[11] Patent Number: 4,950,632

[45] Date of Patent: Aug. 21, 1990

[54] CATALYSTS AND CATALYST SUPPORTS, WITH INORGANIC NITRATES, FOR OLEFIN DIMERIZATION

[75] Inventor: Charles A. Drake, Nowata, Okla.

[73] Assignee: Phillips Petroleum Company, Bartlesville, Okla.

[21] Appl. No.: 375,563

[22] Filed: Jul. 5, 1989

[51] Int. Cl.$^5$ .................... B01J 27/232; B01J 23/04; B01J 23/02; C07C 2/24

[52] U.S. Cl. .................................. 502/184; 502/174; 502/183; 502/185; 502/439; 585/516

[58] Field of Search ............... 502/174, 184, 185, 439, 502/183; 423/421

[56] References Cited

U.S. PATENT DOCUMENTS

| | | | |
|---|---|---|---|
| 3,756,963 | 9/1973 | Forni | 502/167 |
| 3,853,786 | 12/1974 | Forni et al. | 502/174 |
| 4,544,790 | 10/1985 | Drake | 585/516 |
| 4,656,154 | 4/1987 | Drake | 502/174 |
| 4,661,466 | 4/1987 | Drake et al. | 502/184 |
| 4,774,215 | 9/1988 | Drake et al. | 502/184 |
| 4,810,688 | 3/1989 | Ewert et al. | 502/174 |
| 4,895,819 | 1/1990 | Drake | 502/439 |

*Primary Examiner*—Paul E. Konopka
*Attorney, Agent, or Firm*—Lynda S. Jolly

[57] ABSTRACT

This invention concerns catalyst systems for olefin dimerization wherein said catalyst system comprises at least one elemental alkali metal catalyst, supported on an alkali metal carbonate support, wherein said support includes an inorganic nitrate. This invention further concerns processes for the dimerization of olefins. The catalytic support can optionally comprise a carbonaceous compound(s), an inorganic oxide(s), or a mixture thereof. Furthermore, the catalyst system optionally can comprise at least one promoter selected from the group consisting of elemental copper, elemental cobalt, finely divided stainless steel, finely divided glass, or mixtures thereof.

13 Claims, No Drawings

CATALYSTS AND CATALYST SUPPORTS, WITH INORGANIC NITRATES, FOR OLEFIN DIMERIZATION

BACKGROUND OF THE INVENTION

This invention relates to alkali metal carbonate supported elemental alkali metal catalysts. It is known in the art to prepare an alkali metal carbonate catalyst support by making a thick paste and eventually forming a pelletized, tabletted, and/or granular support. It is also known in the art to use an alkali metal carbonate to support an elemental alkali metal to form a catalyst system useful to promote olefin dimerization. However, these types of catalysts and catalyst supports can suffer from low selectivity for the desired reaction product(s). Thus, it can be difficult to process and obtain economically useful amounts of the reaction product(s) that are desired.

SUMMARY OF THE INVENTION

It is an object of this invention to provide a simplified process to prepare an improved alkali metal carbonate catalyst support.

It is a further object of this invention to provide a method to prepare an improved alkali metal carbonate supported elemental alkali metal catalyst system.

It is yet another object of this invention to provide an improved catalyst system for the dimerization of olefins.

Accordingly, the present invention provides an alkali metal carbonate catalyst support which is prepared from a thick paste comprising an alkali metal carbonate, water, and an inorganic nitrate. The resultant thick paste is formed into a particulate product and calcined to give an improved catalyst support.

In another embodiment of the invention, an elemental alkali metal is supported on the inventive alkali metal carbonate support to form an improved catalyst system for olefin dimerization. The novel catalyst system, when used to dimerize olefins, provides improved selectivity to the desired reaction product(s).

DESCRIPTION OF THE PREFERRED EMBODIMENTS

The present invention provides a process to prepare a catalyst support which comprises the steps of forming a thick paste comprising an alkali metal carbonate, water, and an inorganic nitrate; forming a particulate product from said paste; and calcining said particulate product. The particulate product can be formed by grinding and seiving prior to calcining or it can be formed into an extrudate, pellets, tablets, pills, or any other granular form prior to calcining.

In accordance with one embodiment of the invention, the thick paste comprising an alkali metal carbonate, water, and an inorganic nitrate can further comprise a carbonaceous compound.

In accordance with a further embodiment of the invention, the thick paste comprising an alkali metal carbonate, water, and an inorganic nitrate can further comprise a non-acidic inorganic oxide.

In accordance with yet another embodiment of the invention, the previously prepared particulate alkali metal carbonate catalyst support can be contacted with at least one elemental alkali metal to produce a catalyst composition.

In accordance with yet a further embodiment of the invention, the alkali metal carbonate catalyst support and the elemental alkali metal catalyst composition can be contacted with at least one promoter.

SUPPORTS

Commerically available alkali metal carbonate in the form of powder, granules, or the like, is mixed with an inorganic nitrate and sufficient water to form a thick paste. This thick paste usually comprises from about 1 to about 50 weight percent of inorganic nitrate, based upon the total weight of the alkali metal carbonate, and sufficient water to dissolve the inorganic nitrate, and yet not dissolve the alkali metal carbonate. The amount of water sufficient to form a thick paste, wherein the inorganic nitrate is dissolved and the alkali metal carbonate is not dissolved, is based on the solubility of the inorganic nitrate in, and the temperature of, the water. Preferably, the thick paste comprises from about 3 to about 40 weight percent of inorganic nitrate, and most preferably, the thick paste comprises from about 5 to about 30 weight percent of inorganic nitrate, based upon the total weight of the alkali metal carbonate. Described in another way, the inorganic nitrate can be from about 1 to about 33 weight percent based on the calcined catalyst support. Preferably, the inorganic nitrate can be from about 3 to about 30 weight percent, and most preferably, the inorganic nitrate can be from about 5 to about 23 weight percent, based upon the calcined catalyst support. Too much inorganic nitrate can result in a catalyst with low strength and inferior performance (low conversion and selectivity). Too little inorganic nitrate gives no improvement over potassium carbonate by itself. If too much water is used to form the thick paste and the alkali metal carbonate dissolves, then the processability of the catalyst becomes more difficult (due to the excess water that must be removed). If too little water is used, the inorganic nitrate will not dissolve and can cause nonhomogeneous catalyst mixture with resulting poor catalyst performance. Furthermore, if too little or too much water is used, formation of a particulate product can be difficult.

Any alkali metal carbonate can be used in the preparation of the catalyst support. Preferably, sodium carbonate or potassium carbonate is used, for ease of use and common availability.

Any inorganic nitrate can be used in the preparation of the catalyst support. Suitable inorganic nitrates include, but are not limited to, cadmium nitrate, cesium nitrate, lead nitrate, lithium nitrate, potassium nitrate, rubidium nitrate, silver nitrate, sodium nitrate, and mixtures thereof. Preferably, sodium nitrate and potassium nitrate are used and most preferably, potassium nitrate is used, for ease of use, common availability, and compatability with the alkali metal carbonate.

The thick paste can then be formed into a particulate product prior to calcining. The paste can be formed into an extrudate using an extruder. The extrudate can be any diameter, but for best catalytic activity and ease of handling and processability, the extrudate is from about 1/16 to about ¼ inch in diameter. After the extrudate passes through the die, the extrudate can be cut into uniform lengths, if desired. However, uniform lengths are not always necessary, so the extrudate can be allowed to break on its own, into any length. If the extrudate is allowed to break on its own, it will usually have a length of about 2 to about 7 times the diameter width. Usually, the extrudate is allowed to break of its own accord because of ease of manufacture.

The thick paste after drying and granulation can also be formed into tablets using a die press, a punch press, or a pelleting machine. Tablets are usually very uniform in size. Tablets look similar to an extrudate, except the two ends of each cylindrical tablet are convex, not blunt.

The thick paste can also be formed into pellets and/or pills. Pellets and pills can be defined as any other type of form that are not prepared using an extruder, a die press, punch press, or pelleting machine. One example of an apparatus used to make pellets or pills is a disk spherudizer. A disk spherudizer, or disk pelletizer, is a flat, circular disk with a lip perpendicularly attached around the circumference of the disk. The disk is mounted at an angle and rotates; scrapers are stationarily mounted above the disk. The disk rotating speed, angle of the disk, solids feed rate onto the disk, and ratio of liquids to solids all control the diameter of the pellets. Usually, the solids and liquids are not mixed prior to introduction onto the disk, but they can be pre-mixed.

Another method of forming a particulate product from the thick paste is to oven dry the thick paste under conditions of time and temperature sufficient to insure that substantially all of the water has been driven off. The dried paste can then be broken into pieces and fractionated by suitable means such as, for example, by passing through the appropriate mesh size screen seives to recover a desired particle size fraction.

The alkali metal carbonate/inorganic nitrate support can optionally contain at least one carbonaceous compound. The carbonaceous compound can be added simultaneously with the alkali metal carbonate, inorganic nitrate, and water. For purposes of this disclosure, the term "carbonaceous compound" is intended to include various forms of the element carbon, including, but not limited to carbon black, charcoal, coconut charcoal, amorphous graphite, crystallite graphite, and the like, as well as mixtures of any two or more thereof. Finely divided graphite is presently preferred because it is useful both as a die lubricant for the pelleting process and it imparts improved activity to the finished dimerization catalyst. The carbonaceous compound, if employed, comprises from about 0.1 to about 10 weight percent of the total alkali metal carbonate. Preferably, the carbonaceous compound comprises from about 0.5 to about 4 weight percent, and most preferably, the carbonaceous compound comprises from about 0.8 to about 2 weight percent of the support. Too much of the carbonaceous compound can cause a lower strength support. Too little of the carbonaceous compound can have a detrimental effect on catalyst activity.

The alkali metal carbonate/inorganic nitrate support can also optionally contain at least one non-acidic inorganic oxide. The non-acidic inorganic oxide can be added simultaneously with the alkali metal carbonate, inorganic nitrate, and water. The non-acidic inorganic oxide, if employed, comprises from about 1 to about 10 weight percent of the alkali metal carbonate. Suitable non-acidic inorganic oxides include, but are not limited to, alumina, such as alpha-alumina, silica, and/or silica-alumina; magnesia-titania; thoria; magnesium; titania; zirconia; and mixtures thereof.

Once the catalyst support is formed and dried, it should be calcined in an oxygen containing atmosphere at a temperature in the range of about 80° to about 400° C. In any case, it is preferable that the temperature be less than the decomposition temperature of the inorganic nitrate. If the calcining temperature is above the decomposition temperature of the inorganic nitrate then the inorganic nitrate decomposes to the oxide and the catalyst is not improved. The catalyst support should be calcined for about 5 minutes to about 10 hours, preferably about 3 hours in order to insure complete calcination and through dryness. The catalyst support is then stored under a dry, oxygen-free atmosphere until needed for further treatment.

As used in this disclosure, the terms "alkali metal carbonate/inorganic nitrate support" and "catalyst support" are interchangeable and refer to any of the inventive supports described above. Furthermore, even though the catalyst support is labelled a support, it is possible that the inventive supports may provide or enhance some catalytic activity.

CATALYSTS AND PROMOTERS

Catalysts systems employed in the practice of this invention comprise one of the alkali metal carbonate/inorganic nitrate supports described above, at least one elemental alkali metal catalyst, and optionally one or more of the following additional promoters:
- elemental copper,
- elemental cobalt,
- finely divided stainless steel,
- finely divided glass, and
- mixtures of two or more thereof.

It should be recognized, however, that the catalyst systems of the invention can contain additional components which do not adversely affect the catalyst performance, such as, for example, pigments, dyes, processing aids, inert fillers, binders and the like.

The alkali metals contemplated to be within the scope of the invention include lithium, sodium, potassium, rubidium and cesium. While the proportion of alkali metal combined with the alkali metal carbonate/inorganic nitrate support can vary appreciably, generally at least about one weight percent of alkali metal based on the total weight of treated support will be employed. Generally, about 1 to about 20 weight percent alkali metal will be employed, with about 2 to about 15 weight percent preferred. An alkali metal loading of about 3 to about 10 weight percent based on the total weight of treated support is most preferred for most efficient use of reagents, high catalyst activity and selectivity, and ease of catalyst preparation. Potassium is the preferred elemental alkali metal due to its ready availability as well as relative ease and safety in handling.

The proportion of optional promoter on the alkali metal carbonate support can vary appreciably, but generally, at least one weight percent of the optional promoter based on the total weight of treated support will be employed. The following amounts are provided for additional guidance:

| Promoter | Loading, Weight Percent | | Preferred |
| --- | --- | --- | --- |
| | Broad | Intermediate | |
| Cu | 1–30 | 3–20 | 5–12 |
| Co | 1–50 | 3–25 | 5–15 |
| *SS | 1–80 | 3–60 | 5–50 |
| Glass | 1–50 | 2–25 | 3–15 |

*SS = Stainless Steel

The general procedure for preparation of a catalyst system, after calcining the support, involves heating the alkali metal carbonate/inorganic nitrate support to a temperature in the range of about 80° to about 350° C. Preferably a temperature slightly above the melting point of the particular alkali metal employed, and below the decomposition temperature of the inorganic nitrate is used. After heating the particulate support, the particulate support is contacted with at least one elemental alkali metal in a dry, oxygen-free atmosphere, such as, for example $N_2$, Ar, or the like, at a temperature sufficient to cause the alkali metal to melt, and yet below the decomposition temperature of the inorganic nitrate. The contacting, which is done in an oxygen-free atmosphere, is preferably carried out with suitable mixing to ensure even distribution. Suitable temperatures for the contacting step will vary with the particular alkali metal employed. For example, with elemental potassium, temperatures in the range of about 80° to about 100° C. are preferred, while with elemental sodium, temperatures in the range of about 100° to about 140° C. are preferred.

While the alkali metal treated support is maintained at or above the melting point of the particular alkali metal used, any desired promoter(s), such as, for example, finely divided stainless steel or elemental copper, can be gradually added while the treated catalyst is continuously stirred. The catalyst system is then ready to be charged to the reactor.

Optionally, the alkali metal carbonate/inorganic nitrate support, once elemental alkali metal and any desired promoters have been deposited thereon, can be subjected to a subsequent heating step, in an oxygen-free atmosphere, to ensure as uniform a distribution as possible of the various promoters on the surface of the alkali metal carbonate/inorganic nitrate support. Thus, the finished catalyst can be subjected to a temperature in the range of at least about 80° C. for a time in the range of about 0.1 to 4 hours. A temperature in the range of about 150° to about 250° C. for a time in the range of about 0.5 to about 2 hours is presently preferred for the most uniform distribution.

Optionally, prior to charging the reactor, the catalyst system can be mixed with an inert substance to dilute the catalyst system and decrease the rate of olefin dimerization. Any inert substance which has no catalytic activity in an olefin dimerization reaction can be used. One example of such an inert substance is glass beads.

As indicated by the variety of supports, alkali metal components, and promoters included within the scope of the invention, numerous catalyst combinations are possible. Any combination of the alkali metal and optional promoters disclosed can be supported on any alkali metal carbonate/inorganic nitrate support disclosed. Some possible combinations are described in detail in the examples which follow. The combination of support, alkali metal and promoter(s) which one may choose to employ will depend on a variety of variables such as, for example, reactor configuration, reaction temperature and pressure, olefin feed employed, rate of olefin feed, and conversions desired.

REACTANTS

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include both self-reation and "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

REACTION CONDITIONS

The dimerization reaction of the invention can be carried out using either batch or continuous types of operation, although the catalysts of the invention are particularly well suited for continuous, fixed bed, operation. Suitable equipment such as for example autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 170° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressure of about 1,000 to about 4,000 psig most preferred in order to achieve a good balance between reaction rate and minimize equipment and operating costs necessitated by very high reaction pressures.

If the reaction is carried out in the liquid phase, solvents or diluents for the reactants can be used. Saturated aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors such as for example the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

PRODUCTS

The olefinic products of the invention have established utility in a wide variety of applications such as for example as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

EXAMPLES

In each of the following Examples, typically, the dimerization of propylene was carried out in a steam heated 316 stainless steel tubular reactor ($\frac{1}{2}'' \times 20''$). The catalyst system, bounded above and below by small volumes of glass beads, was combined with 25 grams of an inert substance, i.e., no dimerization catalytic activity, to dilute the catalyst system and thus reduce and control the reaction rate. The contents of the tubular reactor were heated to the reaction temperature of about 160° C. at about 1500 psig and propylene was pumped into the reactor at a rate of about 120 mL/hr. After about 1.5 hours of reaction time and each one hour thereafter for the following 6 hours, a sample was collected and analyzed by gas liquid chromatography (glc). The summarized results represent the analysis of the last dimerization sample collected.

EXAMPLE

The granular catalyst supports were prepared from commerically available, anhydrous potassium carbonate (ACS reagent grade), graphite (ACS reagent grade), and deionized water. The potassium carbonate and graphite (1 weight percent of potassium carbonate) were then mixed together with either potassium acetate (ACS reagent grade) or potassium nitrate (ACS reagent grade), as the tested components. This resulting mixture was made into a thick paste by the addition of water. Usually about 2 milliliters of water were added to about 1 gram of the mixture in order to form the paste. The thick paste was thoroughly mixed and then dried. The dried paste was then ground to about 6 mesh and calcined at about 350° C. for about 3 hours in an oxygen containing atmosphere.

The resulting support was allowed to cool, in an oxygen-free atmosphere, to about 85° C., at which time about 5 weight percent of elemental potassium, based on the calcined catalyst support weight, was added. The catalyst system was then heated to 200° C. for 1 hour and then stored in a dry, inert atmosphere until used.

The catalysts and the results of the corresponding propylene dimerization reactions are summarized in Table One. As used in these Examples, 4-methyl-1-pentene is designated as 4MP1 and 4-methyl-2-pentene is designated as 4MP2.

TABLE ONE

| Run | Additional Support Component | Propylene Conv. % | Product to 4MP1% | 4MP1 4MP2 |
|---|---|---|---|---|
| 1 | None | 13.8 | 88.7 | 24.7 |
| 2 | 10% K$_2$C$_2$H$_3$O$_2$ | 12.8 | 88.4 | 23.2 |
| 3 | 20% KNO$_3$ | 11.8 | 90.1 | 37.3 |
| 4 | 10% KNO$_3$ | 12.8 | 90.0 | 38.5 |

After the propylene dimerization, the catalyst systems from Runs 1, 3, and 4 were removed from the dimerization reactor and examined. Each catalyst system showed some fines, however, the control catalyst, Run 1, had an apparent breakdown of the catalyst system, as indicated by the considerable amount of structural degradation of the catalyst system. The other two Runs that were examined did not have any such breakdown of the catalyst system.

Comparison of the percent selectivity to 4MP1, and the 4MP1/4MP2 product ratio indicate that catalyst systems made with an inorganic nitrate produce better results than catalyst systems made without an inorganic nitrate. Consequently, the addition of an inorganic nitrate, to a catalyst support, for a catalyst system, for olefin dimerization, shows an improvement over similar catalyst systems prepared without an inorganic nitrate in the catalyst support.

The Examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A process for the preparation of a catalyst support comprising:
   (a) preparing a thick paste comprising an alkali metal carbonate; from about 1 to about 50 weight percent inorganic nitrate, based on the weight of the alkali metal carbonate; and water, at a temperature and in an amount sufficient to dissolve the inorganic nitrate, but insufficient to dissolve the alkali metal carbonate; and
   (b) forming a particulate product from said paste; and
   (c) calcining said particulate product at a temperature less than the decomposition temperature of said inorganic nitrate.

2. A process according to claim 1 wherein said alkali metal carbonate is selected from the group consisting of sodium carbonate, potassium carbonate, and mixtures thereof.

3. A process according to claim 1 wherein said inorganic nitrate is selected from the group consisting of cadmium nitrate, cesium nitrate, lead nitrate, lithium nitrate, potassium nitrate, rubidium nitrate, silver nitrate, sodium nitrate, and mixtures thereof.

4. A process according to claim 1 wherein said thick paste further comprises a carbonaceous compound which is from about 0.1 to about 10 weight percent of the alkali metal carbonate, and is selected from the group consisting of carbon black, charcoal, coconut charcoal, amorphous graphite, crystallite graphite, and mixtures thereof.

5. A process according to claim 1 wherein said thick paste further comprises a non-acidic inorganic oxide which is from about 1 to about 10 weight percent of said alkali metal carbonate, and is selected from the group consisting of alpha-alumina, silica, silica-alumina, magnesia-titania, thoria, magnesia, titania, zirconia, and mixtures thereof.

6. A process according to claim 1 wherein said particulate product is formed by:
   (a) drying said thick paste under conditions suitable to remove essentially all water from said thick paste, and
   (b) grinding the thus-dried thick paste to form said particulate product.

7. A process according to claim 1 wherein said particulate product is calcined in an oxygen containing atmosphere at a temperature below the decomposition temperature of said inorganic nitrate for a time within the range of from about 5 minutes to about 10 hours.

8. A process according to claim 1 further comprising contacting said catalyst support with at least one elemental alkali metal in an oxygen free atmosphere at a temperature sufficient to cause the alkali metal to melt, and to form a catalyst system.

9. A process according to claim 8 further comprising contacting said catalyst system with at least one promoter selected from the group consisting of finely divided stainless steel, elemental copper, elemental cobalt, finely divided glass and mixtures thereof.

10. A process according to claim 8 wherein said elemental alkali metal is selected from the group consisting of sodium, potassium, and mixtures thereof.

11. A process according to claim 8 wherein said elemental alkali metal is from about 1 to about 20 weight percent of said catalyst support.

12. A catalyst produced by the process of claim 8.

13. A catalyst produced by the process of claim 9.

* * * * *